United States Patent
Hitzl et al.

(10) Patent No.: US 8,034,778 B2
(45) Date of Patent: Oct. 11, 2011

(54) NEUROPROTECTIVE COMPOUNDS AND USES THEREOF

(75) Inventors: Monika Hitzl, Salzburg (AT); Herbert Mossler, Seekirchen (AT); Heinz Schnait, Seewalchen (AT)

(73) Assignee: Ever Neuro Pharma GmbH, Unterach am Attersee (AT)

( * ) Notice: Subject to any disclaimer, the term of this patent is extended or adjusted under 35 U.S.C. 154(b) by 299 days.

(21) Appl. No.: 12/299,463

(22) PCT Filed: May 3, 2007

(86) PCT No.: PCT/EP2007/003906
§ 371 (c)(1),
(2), (4) Date: Nov. 3, 2008

(87) PCT Pub. No.: WO2007/128493
PCT Pub. Date: Nov. 15, 2007

(65) Prior Publication Data
US 2009/0105159 A1 Apr. 23, 2009

(30) Foreign Application Priority Data
May 3, 2006 (EP) .................................. 06450065

(51) Int. Cl.
*A61K 38/00* (2006.01)
*A61K 38/07* (2006.01)
*C07K 5/00* (2006.01)
*C07K 5/10* (2006.01)

(52) U.S. Cl. ....... 514/18.1; 514/21.9; 530/300; 530/330

(58) Field of Classification Search ........................ None
See application file for complete search history.

(56) References Cited

FOREIGN PATENT DOCUMENTS

| EP | 452299 A1 | 10/1991 |
|---|---|---|
| EP | 452299 B1 | 6/1997 |
| WO | WO 97/11963 | 4/1997 |
| WO | WO 01/29067 | 4/2001 |
| WO | WO 01/96364 | 12/2001 |
| WO | WO 2004/011650 | 2/2004 |

OTHER PUBLICATIONS

Doraiswamy "Non-cholinergic strategies for treating and preventing Alzheimer's disease," *CNS Drugs*, 16 (12): 811-824, 2002.
International Search Report and Written Opinion, issued in Int. App. No. PCT/EP2007/003906, mail date Aug. 8, 2007.
Merrifield, "Solid phase peptide synthesis. I. The synthesis of a tetrapeptide," *J. Am. Chem. Soc.*, 85: 2149-2154, 1963.
Mosmann, "Rapid colorimetric assay for cullar growth and survival: application to proliferation and cytotoxicity assays," *J. of Immunological Methods*, 65 (1-2): 55-63, 1983.
Partial European Search Report, issued in Int. App. No. EP 06450065, mail date Nov. 20, 2006.
Sandrin et al., "Natural human anti-Gal. alpha. (1-3)gal antibodies react with human mucin peptides," *Glycoconjugate Journal*, 14 (1): 97-105, 1997.
Schauer et al., "Neuroprotection of cerebrolysin in tissue culture models of brain ischemia: post lesion application indicates a wide therapeutic window," *J. of Neural Transmission*, 113 (7): 855-868, 2006.

*Primary Examiner* — Daniel E Kolker
*Assistant Examiner* — Aditi Dutt
(74) *Attorney, Agent, or Firm* — Fulbright & Jaworski LLP

(57) ABSTRACT

The present invention relates to a neuroprotective compound consisting of the amino acid sequence DLHW.

8 Claims, 1 Drawing Sheet

```
                        SEQUENCE LISTING

<160> NUMBER OF SEQ ID NOS: 5

<210> SEQ ID NO 1
<211> LENGTH: 10
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (1)..(3)
<223> OTHER INFORMATION: Xaa can be none or any naturally occurring
      amino acid
<220> FEATURE:
<221> NAME/KEY: misc_feature
<222> LOCATION: (8)..(10)
<223> OTHER INFORMATION: Xaa can be none or any naturally occurring
      amino acid

<400> SEQUENCE: 1

Xaa Xaa Xaa Asp Leu His Trp Xaa Xaa Xaa
1               5                   10

<210> SEQ ID NO 2
<211> LENGTH: 4
<212> TYPE: PRT
<213> ORGANISM: Artificial
<220> FEATURE:
<223> OTHER INFORMATION: Synthetic peptide

<400> SEQUENCE: 2

Asp Leu His Trp
1

<210> SEQ ID NO 3
<211> LENGTH: 6
<212> TYPE: PRT
<213> ORGANISM: Artificial
<220> FEATURE:
<223> OTHER INFORMATION: Synthetic peptide

<400> SEQUENCE: 3

Asn Ile Val Thr Pro Arg
1               5
```

```
<210> SEQ ID NO 4
<211> LENGTH: 6
<212> TYPE: PRT
<213> ORGANISM: Artificial
<220> FEATURE:
<223> OTHER INFORMATION: Synthetic peptide

<400> SEQUENCE: 4

His Gly Phe Leu Pro Arg
1               5

<210> SEQ ID NO 5
<211> LENGTH: 7
<212> TYPE: PRT
<213> ORGANISM: Artificial
<220> FEATURE:
<223> OTHER INFORMATION: Synthetic peptide

<400> SEQUENCE: 5

Asn Met Val Pro Phe Pro Arg
1               5
```

NEUROPROTECTIVE COMPOUNDS AND USES THEREOF

Figure 1:
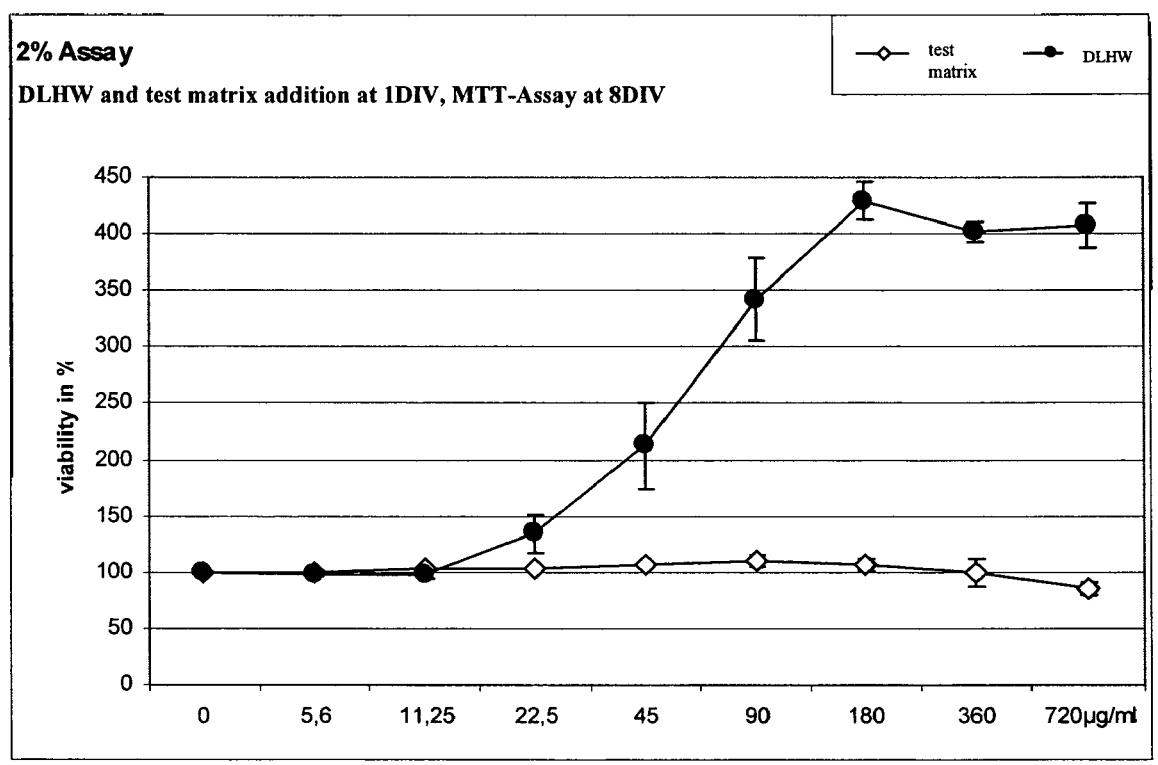

This application is a national phase application under 35 U.S.C. §371 of International Application No. PCT/EP2007/003906 filed 3 May 2007, which claims priority to European Application No. 06450065.5 filed 3 May 2006. The entire text of each of the above-referenced disclosures is specifically incorporated herein by reference without disclaimer.

The present invention relates to a neuroprotective compound and uses thereof.

The population in the industrialised countries is rapidly ageing due to a greater life expectancy, and an ever-increasing number of people are afflicted with neurodegenerative diseases making a global issue out of these diseases.

Neurodegenerative diseases result from the gradual and progressive loss of neural cells, leading to nervous system dysfunction and may have next to ageing various causes (e.g. environmental influences, genetic defects). Till now more than 600 neurologic disorders are known.

The major known risk factors for neurodegenerative disease include certain genetic polymorphisms and increasing age. Other possible causes may include gender, poor education, endocrine conditions, oxidative stress, inflammation, stroke, hypertension, diabetes, smoking, head trauma, depression, infection, tumors, vitamin deficiencies, immune and metabolic conditions, and chemical exposure. Because the pathogenesis of many of these diseases remains unknown, also the role of environmental factors in these diseases may be considered. An overview of neurodegenerative diseases can be found, for instance, in "Neurodegenerative Diseases: Neurobiology, Pathogenesis and Therapeutics" (M. Flint Beal, Anthony E. Lang, and Albert C. Ludolph; Cambridge University Press; 2005).

In order to treat neurodegenerative diseases several medicaments comprising one or more active compounds like Piracetam, Nimotop, Vinpocetin, Gliatilin, Cerebrolysin, Cytoflavin etc. are regularly employed. The compounds known in the art have varying modes of action. Cerebrolysin, for instance, a peptide based drug produced from purified animal brain proteins by standardized enzymatic breakdown, is exerting nerve growth factor like activity on neurons from dorsal root ganglia, neurotrophic and neuroprotective effects.

In the prior art several therapeutic substances with neuroprotective properties are known. The WO 01/29067, for instance, relates to the tetrapeptide L-alanyl-L-glutamyl-L-asparagyl-L-proline which as a biologically active compound stimulates the functional activity of neurones. The application of L-Ala-L-Glu-L-Asp-L-Pro tetrapeptide in medicine is proposed for the preparation of drugs stimulating the functional activity of neurones.

The US 2004/102370 relates to peptides comprising the essential tetrameric peptide structural unit Xaa-Xaa-Xaa-Xaa in which Xaa at position 1 represents Glu or Asp, Xaa at position 2 represents any amino acid, Xaa at position 3 represents any amino acid and Xaa at position 4 represents Glu or Asp. Said peptides are used to treat neurodegenerative diseases and nerve damages, and are described to be stimulators of axonal regeneration and survival.

It is an object of the present invention to provide novel compounds to be used in the course of the treatment of neurodegenerative diseases and to improve memory in healthy people.

Therefore the present invention relates to neuroprotective compound consisting of the amino acid sequence DLHW (SEQ ID NO:2).

The amino acid residue abbreviations are those commonly used in the art, namely D stands for Aspartic acid (Asp), L stands for Leucine (Leu), H stands for Histidine (His) and W stands for Tryptophan (Trp).

The compound according to the present invention may exhibit neuroprotective and neurotrophic properties by affecting the viability of neural cells. These properties allow to increase the viability of neuronal cells. Said compound, which may also be part of a protein, conjugated to a protein, conjugated to other molecules etc., shows similar neuroprotective properties like other well known neuroprotective agents known in the art. The compound according to the present invention can be administered together (e.g. in one single dosage form) or in parallel (e.g. different application routes and/or sites) with other active components or as a single active component.

If the compound according to the present invention is part of or conjugated or fused to a protein or conjugated to another molecule (e.g. glycan), said compound has to be exposed on the surface of said protein or said conjugated molecule in order to activate or inactivate signal transduction cascades. The accessibility of the peptide according to the present invention can be determined by computational protein design or by experimental approaches.

Preferred conjugation or fusion partners of the compound of the present invention are molecules which may allow to target the compound to a specific site in the body of an individual after its administration. Fusion partners may be, for instance, antibodies directed to certain cells in an individual.

As used herein, the term "neuroprotective" compound or "neuroprotective" composition refers to a compound (or to a mixture of compounds) that protects a neuronal cell from a toxic substance, stabilizes the cell membrane of a neuronal cell and/or helps in the normalization of neuronal cell functions. A "neuroprotective" compound thereby prevents the loss of viability or functions of neuronal cells in stressing conditions. Neuroprotective activity may be determined, by a cell culture assay (measuring the viability of neuronal cells, e.g. by the MTT assay (Mosmann T (1983), J. Immuno. Methods 65: 55-61)).

The compounds of the present invention exhibit also neurotrophic and/or neurogenic properties. This means that the compounds of the invention can also stimulate the growth of neuronal cells.

The basic structure of the compound according to the present invention, which is formed by amino acids, is preferably synthesised chemically according to methods known in the art, e.g. by the method developed by Merrifield et al. (Merrifield, R. B. (1963) J. Am. Chem. Soc. 85, 2149-2154; solid phase peptide synthesis).

The solid phase peptide synthesis method introduced by Merrifield in 1963, for instance, involves the attachment of a growing peptide chain to a solid support. An amino acid corresponding to the C-terminal of the target peptide is covalently attached to an insoluble polymeric support (the "resin"). The next amino acid, with a protected alpha-amino acid, is activated and reacted with the resin-bound amino acid to yield an amino-protected dipeptide on the resin. The amino-protecting group is removed and chain extension is continued with the third and subsequent protected amino acids. After the target protected peptide chain has been built up the resin is cleaved by suitable chemical means thereby releasing the crude peptide product into solution (for solid phase peptide synthesis methods and other peptide synthesis methods see also Fields, G. B. (ed.), *Solid-PhasePeptide Synthesis in Methods in ENZYMOLOGY*, Vol. 289, Academic Press, San Diego (1997); Bodansky, M., Bodansky, A., The practice of peptide synthesis (2nd edn.), Springer Verlag, Berlin (1995); Pennington, M. W., Dunn, B. M. (eds), Peptide Synthesis Protocols, in Methods in Molecular Biology, Vol. 35, Humana Press Inc., Totowa (1994); Grant, G. A. (ed.), Synthetic peptides: a user's guide, W. H. Freemann & Co., New York (1992)).

The inorganic cation at the C-terminal end of the compound according to the present invention may be an alkali metal or alkali earth metal cation, preferably a lithium, sodium, potassium, magnesium or calcium cation.

These inorganic cations are regularly used to prepare salts of pharmaceutically active substances.

The organic cation may be a quaternary ammonium ion.

If the N-terminal end of the compound according to the present invention comprises a positive charge, said charge may be preferably compensated by an equivalent of an inorganic or organic anion. The organic anion can be, for instance, acetate anion.

According to another preferred embodiment of the present invention the alkyl residue comprises less than 30, preferably less than 20, more preferably less than 10, carbon atoms.

A fatty acid, for instance, esterified to the compound according to the present invention may change its physical properties leading to more hydrophobic compound.

According to another preferred embodiment of the present invention the compound with the formula (I) may be a repeating unit of a higher molecular molecule. Said molecule may comprise 2, 3, 4, 5, 6, 10 or more of the compounds according to the present invention. Such a high molecular molecule may exhibit a significant higher efficacy when administered to an individual than a single compound molecule.

Another aspect of the present invention relates to a pharmaceutical composition comprising a compound according to the present invention and optionally at least one pharmaceutically acceptable excipient and/or carrier.

The compound according to the present invention may be formulated in a pharmaceutical preparation, which can be administered to a patient for preventing or treating a cerebral disease, in particular a neurodegenerative disease. The pharmaceutical preparation may further comprise pharmaceutically acceptable excipients and/or carriers. Suitable excipients and carriers are well known in the art (see e.g. "Handbook of Pharmaceutical Excipients", 5th Edition by Raymond C. Rowe, Paul J. Sheskey, Siân C. Owen (2005), APhA Publications).

According to a preferred embodiment of the present invention the composition may further comprise at least one additional pharmaceutically active component.

The pharmaceutical preparation according to the present invention may comprise next to the neuroprotective compound according to the present invention further active components, which may exhibit similar properties when administered to an individual or which may cause other reactions in the treated patient.

Said at least one pharmaceutically active component is preferably selected from the group consisting of the tetrapeptide L-alanyl-L-glutamyl-L-asparagyl-L-proline (see e.g. WO 01/29067) and cerebrolysin (see e.g. EP 452 299).

According to the present invention, e.g., antioxidants like vitamins may be considered as further active components because antioxidants inhibit oxidation or suppress reactions promoted by oxygen, oxygen free radicals, oxygen reactive species including peroxides. Antioxidants, especially lipid-soluble antioxidants, can be absorbed into the cell membrane to neutralize oxygen radicals and thereby protect the membrane. The antioxidants useful in the present invention are preferably vitamin antioxidants that may be selected from the group consisting of all forms of Vitamin A including retinal and 3,4-didehydroretinal, all forms of carotene such as alpha-carotene, beta-carotene, gamma-carotene, delta-carotene, all forms of Vitamin C (D-ascorbic acid, L-ascorbic acid), all forms of tocopherol such as Vitamin E (Alpha-tocopherol, 3,4-dihydro-2,5,7,8-tetramethyl-2-(4,8,12-trimethyltri-decyl)-2H-1-benzopyran-6-ol), beta-tocopherol, gamma-tocopherol, delta-tocopherol, tocoquinone, tocotrienol and Vitamin E esters which readily undergo hydrolysis to Vitamin E such as Vitamin E acetate and Vitamin E succinate, and pharmaceutically acceptable Vitamin E salts such as Vitamin E phosphate, prodrugs of Vitamin A, carotene, Vitamin C, and Vitamin E, pharmaceutically acceptable salts of Vitamin A, carotene, Vitamin C, and Vitamin E, and the like, and mixtures thereof.

According to another preferred embodiment of the present invention the composition is provided for intravenous, intramuscular, spinal, epidural, transdermal, parenteral, oral, enteral, intranasal or rectal administration.

Depending on the route of administration the pharmaceutical composition according to the present invention may be formulated, for instance, as tablets, capsules, liquids, infusion and suppositories (see e.g. "Pharmaceutical Formulation Development of Compounds" by Sven Frokjaer (1999), CRC; "Handbook of Pharmaceutical Manufacturing Formulations" by Sarfaraz K. Niazi (2004), CRC).

The compounds are preferably comprised in the composition in an amount between 0.1 µg/g to 100 mg/g, preferably 1 µg/g to 80 mg/g.

Another aspect of the present invention relates to the use of a compound with neuroprotective activity comprising a molecule with the formula (I) (SEQ ID NO:1):

$X_n$—DLHW—$Y_m$ wherein

X and Y represent an amino acid residue and n and m an integer between 0 and 3 and as defined above for the manufacture of a medicament for the treatment and/or prevention of a neurodegenerative disease.

According to the present invention all compounds with the formula (I) exhibiting neuroprotective activity may be used for manufacturing a medicament for the treatment and/or prevention of neurodegenerative diseases.

Neuroprotective activity may be determined, e.g., by the MTT assay (Mosmann T (1983), J. Immuno. Methods 65: 55-61). The MTT assay is a cell viability test. In metabolic active cells (e.g. neuronal cells), the enzyme succinate dehydrogenase breaks down MTT to purple blue formazan particles. All viable cells treated with MTT turn purple blue in colour. All treated cells that have died, are unable to break down the MTT and therefore, their colours do not change. The rate of colour change, which is a measure of the amount of formazan particles, can be measured by reading the absorbance using a plate reader. The viability is expressed as percentage of control.

If the C-terminus of compound (I) is negatively charged said charge may be compensated by an equivalent of an inorganic or organic cation or an alkyl residue.

The compound according to the present invention may exhibit neuroprotective and neurotrophic properties by affecting the viability of neural cells. These properties allow to increase the viability of neuronal cells. Said compound, which may also be part of a protein, conjugated to a protein, conjugated to other molecules etc., shows similar neuroprotective properties like other well known neuroprotective agents known in the art. The compound according to the present invention can be administered together (e.g. in one single dosage form) or in parallel (e.g. different application routes and/or sites) with other active components or as a single active component.

If the compound according to the present invention is part of or conjugated or fused to a protein or conjugated to another molecule (e.g. glycan), said compound has to be exposed on the surface of said protein or said conjugated molecule in order to activate or inactivate signal transduction cascades. The accessibility of the peptide according to the present invention can be determined by computational protein design or by experimental approaches.

Preferred conjugation or fusion partners of the compound of the present invention are molecules which may allow to target the compound to a specific site in the body of an individual after its administration. Fusion partners may be, for instance, antibodies directed to certain cells in an individual.

The amino acid residue preferably bound to the compound according to the present invention can be selected from the group of all known naturally occurring amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine) or of course from "non-standard" amino acids like selenocysteine, pyrrolysine, taurine, GABA (gamma-aminobutyric acid), lanthionine, 1-amino isobutyric acid, dehydroalanine, dehydroamino-butyric acid, hydroxyproline and ornithine.

The compound according to the present invention is preferably non immunogenic. The term "non immunogenic compound" as used herein refers to a molecule, in particular to a compound, which does substantially not provoke an immune response in vivo when administered to a human or an animal being. This molecule property can be determined by methods known in the art. For instance, if the administration of a molecule according to the present invention to an animal (e.g. rabbit, mouse) provokes in an animal a substantial increase of antibodies directed against said molecule, said molecule is considered as an "immunogenic compound", if, however, substantially no molecule-specific anti-bodies can be induced in an animal or human upon administration of said molecule, it is considered as a "non immunogenic compound". It is important that the compounds according to the present invention are non immunogenic because immunogenic compounds are normally eliminated from the body by the immune system.

The basic structure of the compound according to the present invention, which is formed by amino acids, is preferably synthesised chemically according to methods known in the art, e.g. by the method developed by Merrifield et al. (Merrifield, R. B. (1963) J. Am. Chem. Soc. 85, 2149-2154; solid phase peptide synthesis).

The inorganic cation at the C-terminal end of the compound according to the present invention may be an alkali metal or alkali earth metal cation, preferably a lithium, sodium, potassium, magnesium or calcium cation.

These inorganic cations are regularly used to prepare salts of pharmaceutically active substances.

The organic cation may be a quaternary ammonium ion.

If the N-terminal end of the compound according to the present invention comprises a positive charge, said charge may be preferably compensated by an equivalent of an inorganic or organic anion. The organic anion can be, for instance, acetate anion.

According to another preferred embodiment of the present invention the alkyl residue comprises less than 30, preferably less than 20, more preferably less than 10, carbon atoms.

A fatty acid, for instance, esterified to the compound according to the present invention may change its physical properties leading to more hydrophobic compound.

According to another preferred embodiment of the present invention the compound with the formula (I) may be a repeating unit of a higher molecular molecule. Said molecule may comprise 2, 3, 4, 5, 6, 10 or more of the compounds according to the present invention. Such a high molecular molecule may exhibit a significant higher efficacy when administered to an individual than a single compound molecule.

According to a preferred embodiment of the present invention the compound is a compound according to the present invention as defined above.

The neurodegenerative disease is preferably selected from the group consisting of Alexander disease, Alper's disease, Alzheimer disease, Amyotrophic lateral sclerosis, Ataxia telangiectasia, Canavan disease, Cockayne syndrome, Corticobasal degeneration, Creutzfeldt-Jakob disease, epilepsy, Huntington disease, Kennedy's disease, Krabbe disease, Lewy body dementia, Machado-Joseph disease (Spinocerebellar ataxia type 3), Multiple sclerosis, Multiple System Atrophy, Parkinson disease, Pelizaeus-Merzbacher Disease, Pick's disease, Primary lateral sclerosis, Refsum's disease, Sandhoff disease, Schilder's disease, Spinocerebellar ataxia, Steele-Richardson-Olszewski disease, stroke and Tabes dorsalis.

Next to these preferred neurodegenerative diseases the compounds according to the present invention may also be used to treat other cerebral disorders.

In a preferred embodiment of the present invention the compounds of the present invention may be used for manufacturing a medicament for improving learning-memory capacities in an individual. The administration of the compound of the present invention to an individual, a healthy person or a person suffering from a disease, preferably a neurological disease, leads to a significant improvement of the learning-memory capacities of said person. Thus, the administration of the compounds of the present invention also to healthy individuals results in a memory improvement. A suitable test to show these positive effects in an animal model may be the Morris Water maze test.

In one embodiment of the invention a peptide or protein comprising DLHW can be employed as a drug stimulating cerebral reparative processes and used for the treatment and prevention of trauma-associated cerebral lesions, including the treatment of cerebral lesions after a fracture of the cranial vault, skull base, multiple bone fractures, the treatment for the cerebral lesions in cases of intracranial trauma (e.g. posttraumatic cerebral concussion, cerebral wounds and contusion, subarachnoid, subdural and extradural haemorrhage), the treatment and prevention of traumatic shock, the treatment of the cerebral lesions associated with the impact of radiation, lowered temperature, heat and light, air pressure, electric and ultrahigh frequency current, the treatment and prevention of delayed-onset effects of skull fractures, the treatment and prevention of delayed-onset effects of intracranial trauma, the treatment and prevention of delayed-onset cerebral lesions induced by radiation, complications after surgical and other medical interventions.

In another embodiment of the present invention the compounds according to the present invention may be used as a drug suppressing toxic effects of the neurotrophic agents, stimulating cerebral repair processes and revealing cerebroprotective activity for the treatment and prevention of cerebral lesions after poisoning including the treatment of cerebral lesions after poisoning with therapeutic agents, medicinal and biological compounds, the treatment of the cerebral impairment with agents of non-medical origin, the treatment and prevention of delayed-on-set cerebral lesions induced by poisoning with drugs and non-medical substances.

In another embodiment of the present invention the compounds according to the present invention may be used as a drug with nootropic activity and stimulating cerebral repair processes for the treatment and prevention of mental deficiencies.

In another embodiment of the present invention the compounds according to the present invention may be used for stimulating cerebral repair processes and motional activity for the treatment and prevention of paralytic disorders including the treatment and prevention of hemiplegia, the treatment and prevention of infantile cerebral paralysis, the treatment and prevention of other paralytic syndromes (quadriplegia, paraplegia, diplegia of upper extremities, monoplegia of lower extremities).

In another embodiment of the present invention the compounds according to the present invention may be used as a drug stimulating cerebral repair processes with cerebroprotective activity for the treatment and prevention of cerebral impairments in case of chromosome anomalies including Down's syndrome.

In another embodiment of the present invention the compounds according to the present invention may be used as a drug stimulating cerebral repair processes with cerebroprotective activity for the treatment and prevention of cerebral impairments in case of inflammatory cerebral disorders including the treatment and prevention of cerebral impairments in case of bacterial meningitis including cryptococcus meningitis in AIDS patients, the treatment and prevention of cerebral impairments in case of non-bacterial meningitis, the treatment and prevention of cerebral impairments in case of meningitis of unclear origin, the treatment and prevention of cerebral impairments in case of encephalitis, myelitis and encephalomyelitis, including cerebral toxoplasmosis in AIDS patients, for the treatment and prevention of cerebral impairments in case of intracranial abscesses, for the treatment and prevention of cerebral impairments in case of phlebitis and thrombophlebitis of intracranial venous sinus, for the treatment and prevention of sequalae after intracranial abscesses or purulent infection.

In another embodiment of the present invention the compounds according to the present invention may be used as a drug stimulating cerebral repair processes with cerebroprotective and nootropic activity for the treatment and prevention of cerebral impairments in case of cerebral-vascular disorders including the treatment and prevention of cerebral impairments in case of subarachnoid haemorrhage, treatment and prevention of cerebral impairments in case of cerebral haemorrhage, the treatment and prevention of cerebral impairments in case of occlusion and Stenosis of precerebral arteries, the treatment and prevention of cerebral impairments in case of occlusion of cerebral arteries , the treatment and prevention of cerebral impairments in case of transitory cerebral ischemia, the treatment and prevention of cerebral impairments in case of other cerebral-vascular disorders (acute cerebral-vascular disorders, cerebral atherosclerosis and other generalised cerebral-vascular disorders, hypertension encephalopathy, cerebral aneurysm, cerebral arteritis and non-purulent thrombosis of intracranial venous sinus).

In another embodiment of the present invention the compounds according to the present invention may be used as a drug stimulating cerebral repair processes, having cerebroprotective and nootropic activity for the treatment and prevention of alcoholic psychosis including the treatment and prevention of delirium tremens at abstinence syndrome, the treatment and prevention of alcoholic amnestic syndrome and other alcoholic dementia disorders, the treatment and prevention of pathologic alcoholic intoxication, the treatment and prevention of alcoholic paranoia and alcoholic psychosis of paranoid type.

In another embodiment of the present invention the compounds according to the present invention may be used as a drug stimulating cerebral repair processes, having cerebroprotective and nootropic activity for the treatment and prevention of cerebral impairment in case of alcoholism.

In another embodiment of the present invention the compounds according to the present invention may be used as a drug suppressing toxic effects of neurotropic agents and having cerebroprotective and nootropic activity for the treatment and prevention of drug-induced psychosis including the treatment and prevention of the drug abstinence syndrome, the treatment and prevention of drug-induced paranoid and/or hallucinatory disorders, the treatment and prevention of pathologic intoxication with medical agents, the treatment and prevention of other drug-induced psychic disorders (delirium, dementia, amnestic syndrome and organic affective syndrome).

In another embodiment of the present invention the compounds according to the present invention may be used as a drug suppressing toxic effects of neurotropic agents and having cerebroprotective activity for the treatment and prevention of drug addiction including the treatment and prevention of addiction to opioid agents, the treatment and prevention of addiction to barbiturate, sedative agents and tranquilisers, the treatment and prevention of cocaine addiction, the treatment and prevention of addiction to cannabis and derivatives thereof, the treatment and prevention of addiction to amphetamine and psychostimulating agents, the treatment and prevention of addiction to hallucinogenic agents, treatment and prevention of cerebral impairments caused by drug abuse without drug addiction (abuse of alcohol, tobacco, cannabis, hallucinogens, opioids, cocaine, psychostimulating agents, antidepressants).

In another embodiment of the present invention the compounds according to the present invention may be used as an agent for treatment and prevention of psychogenic symptoms and syndromes including the treatment and prevention of psychogenic physiologic impairments, the treatment and prevention of other psychogenic symptoms and syndromes (stammering and impediments, psychogenic anorexia tics, repeated stereotype movements, inorganic sleep disorders, psychogenic diet disorders, enuresis, psychalgia), the treatment and prevention of acute stress response, the treatment and prevention of reactions induced by psychological directions.

In another embodiment of the present invention the compounds according to the present invention may be used as an agent for treatment and prevention of inorganic psychoses including the treatment and prevention of Schizophrenie disorders, the treatment and prevention of affective psychoses, the treatment and prevention of paranoid conditions, the treatment and prevention of other inorganic psychoses (psychoses of depressive and agitate types, reactive confusion, acute paranoid reactions, psychogenic paranoid psychoses) and non-differentiated psychoses including psychoses induced with cerebral impairments in AIDS patients, the treatment and prevention of infantile psychoses including infantile autism and disintegrative psychoses.

In another embodiment of the present invention the compounds according to the present invention may be used as a drug stimulating cerebral repair processes and having cerebroprotective and nootropic activity for the treatment and prevention of cerebral impairments in case of other cerebral disorders including the treatment and prevention of cerebral impairments in case of cerebral cysts, the treatment and prevention of hypoxic cerebral damage, the treatment and prevention of cerebral impairments in case of intracranial hypertension, the treatment and prevention of cerebral impairments in case of encephalopathy.

In another embodiment of the present invention the compounds according to the present invention may be used as a drug stimulating cerebral repair processes and motional activity, having cerebroprotective and nootropic effects for treatment and prevention of symptoms and syndromes in case of various cerebral disorders including the treatment and prevention of cognitive disorders, memory and attention, impairments (for instance, in case of amnestic diseases, mental deficiency, inorganic psychoses, etc.), the treatment and prevention of aphasia and apraxia (for instance, in case of amnestic diseases, inorganic psychoses, cerebral impairments due to chromosome anomalies, etc.), the treatment and prevention of emotional disorders (for instance, in case of inorganic psychoses, demyelinising cerebral disorders, etc.), the treatment and prevention of psychopathologic syndrome (for instance, in case of transitional organic psychotic conditions, drug-induced psychoses, drug addiction, etc.), the treatment and prevention of asthenic-depressive syndrome (for instance, in case of inorganic psychoses, cerebral impairments due to chromosome anomalies, etc.), the treatment and prevention of delirium syndrome (for instance, in case of drug-induced psychoses and drug addiction, inorganic psychoses, etc.), the treatment and prevention of sleep disorders (for instance, in case of cerebral tumours, transitional organic psychotic conditions, etc.), for treatment and prevention of cerebral-focal syndrome (focal pathologic symptoms) (for instance, in case of cerebral impairments caused by complications of surgical or other medical intervention, demyelinising cerebral disorders, etc.), the treatment and prevention of syndrome of motor disorders (for instance, in case of cerebral tumours, cerebral impairments caused by poisoning, etc.), the treatment and prevention of peripheral neuropathy, preferably diabetic neuropathy.

According to a preferred embodiment of the present invention the medicament further comprises a pharmaceutical acceptable excipient and/or carrier as defined above.

According to another preferred embodiment of the present invention the composition further comprises at least one additional pharmaceutically active component.

Said at least one pharmaceutically active component is preferably selected from the group consisting of the tetrapeptide L-alanyl-L-glutamyl-L-asparagyl-L-proline and cerebrolysin.

The medicament is preferably provided for intravenous, intramuscular, spinal, epidural, transdermal, parenteral, oral, enteral or rectal administration.

According to a preferred embodiment of the present invention the medicament comprises the compound in an amount between 0.1 μg/g to 100 mg/g, preferably 1 μg/g to 80 mg/g.

It is in particular preferred to use as compound a tetrapeptide having the amino acid sequence DLHW (SEQ ID NO:2).

Another aspect of the present invention relates to a method for preventing a break out of a neurodegenerative disease in an individual and for treating an individual suffering from a neurodegenerative disease comprising the administration of a pharmaceutical preparation or of an effective amount of a compound according to the present invention.

The term "effective amount" of a compound as used herein will depend among other factors on the route of administration and physical condition of the individual to be exposed to said compound. Methods for the determination of the effective amount are known to the skilled person.

The neurodegenerative disease is preferably selected from the group consisting of Alexander disease, Alper's disease, Alzheimer disease, Amyotrophic lateral sclerosis, Ataxia telangiectasia, Canavan disease, Cockayne syndrome, Corticobasal degeneration, Creutzfeldt-Jakob disease, epilepsy, Huntington disease, Kennedy's disease, Krabbe disease, Lewy body dementia, Machado-Joseph disease (Spinocerebellar ataxia type 3), Multiple sclerosis, Multiple System Atrophy, Parkinson disease, Pelizaeus-Merzbacher Disease, Pick's disease, Primary lateral sclerosis, Refsum's disease, Sandhoff disease, Schilder's disease, Spinocerebellar ataxia, Steele-Richardson-Olszewski disease, peripheral neuropathy, diabetic neuropathy, stroke and Tabes dorsalis.

According to a preferred embodiment of the present invention the compound is administered to said individual at a dose of 0.1 μg/kg to 20 mg/kg body weight, preferably 0.5 μg/kg to 10 mg/kg body weight.

Another aspect of the present invention relates to a method for cultivating neuronal cells comprising the steps of:
providing a neuronal cell culture,
adding to said culture a compound according to the present invention, and
incubating the compound/culture mixture.

The compound according to the present invention can also be advantageously employed for in vitro purposes for the cultivation of neuronal cells, for instance. Said compound is simply added to cultivation media known in the art.

The compound is preferably comprised in said culture in an amount of 5 μg/ml to 2 mg/ml, preferably 10 μg/ml to 1 mg/ml, more preferably 15 μg/ml to 900 μg/ml, culture medium.

The compound according to the present invention exhibits a neuroprotective effect on neuronal cells in particular when it is comprised in the above mentioned concentration in the culture medium.

The present invention is further illustrated by the following figure and examples without being restricted thereto.

FIG. 1 shows the effects of DLHW in comparison to the test matrix added at 1DIV (first day in vitro) on viability of cortical neurons obtained in the 2% Low Serum Assay with the MTT method. Results shown as mean and SEM of the data in % (control is 100%). Values represent the mean and SEM in % (100%=control) from two independent experiments performed at two days with two identical 96-well plates (n≧8 for each test item concentration and for controls). The unlesioned control is represented by 0 and did not receive any test item.

EXAMPLES

Example 1

The present example using a 2% low serum assay was carried out to evaluate the neuroprotective potential of a peptide DLHW consisting of the amino acid sequence. Effects were evaluated also for the test matrix (6.18 mg/ml NaCl and 0.35 mg/ml KCl).

1.1. Test and Reference Items
1.1.1. Test Items:
Peptides consisting of the amino acid sequence DLHW (SEQ ID NO:2), NIVTPR (SEQ ID NO:3), HGFLPR (SEQ ID NO:4) and NMVPFPR (SEQ ID NO:5) and the test matrix (6.18 mg/ml NaCl and 0.35 mg/ml KCl) as reference, respectively.

1.1.2. Assay Conditions:

Assay: 2% low serum cell culture assay

Cell source: telencephalon neurons from 9-day-old chicken embryos (Lohman Brown hybrid)

Nutrition medium: EMEM with 1 g glucose/l, 2% FCS, 0.01% gentamycin sulfate and 2 mM L-glutamine Group size: 4 independent experiments were performed (n=8 for DLHW (SEQ ID NO:2), NIVTPR (SEQ ID NO:3), HGFLPR (SEQ ID NO:4), NMVPFPR (SEQ ID NO:5) and the test matrix)

Evaluation of the effects:
  MTT viability assay; absorbance (OD) measured with a plate reader Duration of one single experiment:
  8 days 1.2. Findings of the Experiments This example describes the effects of peptides consisting of the amino acid sequences DLHW (SEQ ID NO:2), NIVTPR (SEQ ID NO:3), HGFLPR (SEQ ID NO:4) and NMVPFPR (SEQ ID NO:5) in a validated 2% low serum assay using chicken cortical neurons in vitro. Effects were evaluated also for the test matrix (6.18 mg/ml NaCl and 0.35 mg/ml KCl).

The general conclusions that can be drawn from the results are:

The results obtained displayed a dose response profile, clearly facilitating neuronal viability, reaching a maximum effect height of over 300% in relation to the untreated control. This additionally indicates that the chosen assay is able to undoubtedly assess a dose response profile.

While the test matrix was not able to increase neuronal viability above the extent of the untreated control, the peptide DLHW (SEQ ID NO:2) was clearly exhibiting neuroprotective effects.

In this example DLHW (SEQ ID NO:2) was tested to be an effective compound reaching a high effect magnitude (330% beyond the controls) at relatively low concentrations. The results of the present example show that this small peptide DLHW (SEQ ID NO:2) or compounds comprising said peptide contribute significantly and efficiently to the increase of neuronal viability. In contrast thereto peptides comprising another amino acid sequence did not show these effects.

2. Substances Tested 2.1. Aim of the Experiments

The experiments were performed to assess the neuroprotective effects of a peptide consisting of the amino acid sequence DLHW (SEQ ID NO:2), NIVTPR (SEQ ID NO:3), HGFLPR (SEQ ID NO:4), NMVPFPR (SEQ ID NO:5) and a test matrix.

2.2. Test and Reference Items 2.2.1. Test Items:

2.2.1.1. Test Item (DLHW) (SEQ ID NO:2):

Vehicle for dilution: test matrix (6.18 mg/ml NaCl and 0.35 mg/ml KCl)

Application mode: once at the $1^{st}$ day

Application period: for the whole experiment, i.e. 8 days, from $1^{st}$ day onwards Concentrations: 5.6, 11.25, 22.5, 45, 90, 180, 360 and 720 µg/ml Administration volume: 0.625, 1.25, 2.5, 5, 10, 20, 40, 80 µl/ml medium 2.2.1.2. Test Item (NIVTPR) (SEQ ID NO:3):

Vehicle for dilution: test matrix (6.18 mg/ml NaCl and 0.35 mg/ml KCl)

Application mode: once at the $1^{st}$ day

Application period: for the whole experiment, i.e. 8 days, from $1^{st}$ day onwards Concentrations: 5.6, 11.25, 22.5, 45, 90, 180, 360 and 720 µg/ml Administration volume: 0.625, 1.25, 2.5, 5, 10, 20, 40, 80 µl/ml medium 2.2.1.3. Test Item (HGFLPR) (SEQ ID NO:4):

Vehicle for dilution: test matrix (6.18 mg/ml NaCl and 0.35 mg/ml KCl)

Application mode: once at the $1^{st}$ day

Application period: for the whole experiment, i.e. 8 days, from $1^{st}$ day onwards Concentrations: 5.6, 11.25, 22.5, 45, 90, 180, 360 and 720 µg/ml Administration volume: 0.625, 1.25, 2.5, 5, 10, 20, 40, 80 µl/ml medium 2.2.1.4. Test Item (NMPFPR) (SEQ ID NO:5):

Vehicle for dilution: test matrix (6.18 mg/ml NaCl and 0.35 mg/ml KCl)

Application mode: once at the $1^{st}$ day

Application period: for the whole experiment, i.e. 8 days, from $1^{st}$ day onwards Concentrations: 5.6, 11.25, 22.5, 45, 90, 180, 360 and 720 µg/ml Administration volume: 0.625, 1.25, 2.5, 5, 10, 20, 40, 80 µl/ml medium 2.3. Assay Conditions Cell culture assays: 2% low serum assay Cell source: telencephalon neurons from 9-day-old chicken embryos (Lohman Brown hybrid)

Nutrition medium: EMEM with 1 g glucose/l, 2% FCS, 0.01% gentamycin sulfate and 2mM L-glutamine Group size: 4 independent experiments were performed (n =8for DLHW (SEQ ID NO:2) ant and the test matrix; n =224 for controls)

Evaluation of the effects: MTT viability assay; absorbance (OD) measured with a plate reader Duration of one single experiment: 8 days 3. Methods The analytical procedure used in the present example is a 2% low serum assay using isolated avian cortical neurons. With this in vitro cell culture assay the neuroprotective and/or neurotrophic potential of compounds can be evaluated by determining the viability of living neurons after a distinct time period in culture. The method for measuring the amount of viable neurons is the MTT-assay.

3.1. Test Items

Biological activity of DLHW (SEQ ID NO:2), NIVTPR (SEQ ID NO:3), HGFLPR (SEQ ID NO:4), NMVPFPR (SEQ ID NO:5) and the test matrix (6.18 mg/ml NaCl and 0.35 mg/ml KCl) were investigated using a validated avian cell culture model system.

3.1.1. Preparation of Peptide Stock Solutions

The peptides to be tested were dissolved in the test matrix (6.18 mg/ml NaCl and 0.35 mg/ml KCl).

3.2. Controls

For control purpose neurons never treated with DLHW (SEQ ID NO:2), NIVTPR (SEQ ID NO:3), HGFLPR (SEQ ID NO:4) and NMVPFPR (SEQ ID NO:5) were used.

3.3. Objective of the Analytical Procedure

In this example the peptides containing the amino acid sequences DLHW (SEQ ID NO:2), NIVTPR (SEQ ID NO:3), HGFLPR (SEQ ID NO:4) and NMVPFPR (SEQ ID NO:5) were investigated to evaluate their possible activity to increase the neuronal viability of isolated cortical neurons. The peptide was applied in a concentration of 4.5mg/ml.

3.4. Group Size/Concentrations

To the isolated nerve cells the peptides or test matrix were added once, i.e. at the first day. The 8 concentrations comprising dose range was between 5.6, 11.25, 22.5, 45, 90, 180, 360 and 720 μg/ml medium; the volumes applied were 0.625, 1.25, 2.5, 5, 10, 20, 40, 80 μl/ml medium.

4. Evaluation

4.1. MTT-Viability Assay

Neuronal viability of cultures was determined with the MTT-assay using a plate-reader (570 nm). The MTT-assay is a sensitive assay measuring the mitochondrial dehydrogenase activity in viable cells only. It is performed according to the method described by Mosmann, *J. Immunol. Meth,* 1983, 55-63. This assay is based on the reduction of yellow MTT (3-(4,5-dimethylthiazol-2-yl)-2,5,diphenyl tetrazolium bromide), to dark blue formazan crystals by mitochondrial dehydrogenases (succinate dehydrogenase). Since this reaction is catalysed in living cells only the assay can be used for the quantification of cell viability. For the determination of cell viability MTT solution was added to each well in a final concentration of 0.5 mg/ml. After 2h the MTT containing medium was aspired. Cells were lysed with 3% SDS, formazan crystals dissolved in isopropanol/HCl. To estimate optical density a plate reader (Anthos HT II) was used at wavelength 570 nm. Neuronal viability is expressed as optical densities (ODs).

5. Statistics

To evaluate differences between treated and untreated neurons the students-t-test was used. Differences were considered to be significant when $p \leq 0.05$.

6. Results

This example describes the in vitro neurotrophic/neuroprotective effects of a peptide containing amino acid sequence DLHW (SEQ ID NO:2). Additionally, a test matrix was tested in the 2% low serum assay, using cortical chick neurons.

Effects were evaluated as mentioned for DLHW (SEQ ID NO:2), NIVTPR (SEQ ID NO:3), HGFLPR (SEQ ID NO:4) and NMVPFPR (SEQ ID NO:5). Additionally, the test matrix (6.18 mg/ml NaCl and 0.35 mg/ml KCl) was tested in this assay. Descriptive statistics for each concentration of the peptides and the test matrix, like mean, standard deviation and s.e.m., are shown in tables 2 and 3 as well as in FIG. 1. Table 4 summarizes the p-values obtained with the students-t-test, statistically evaluating differences between the untreated controls and each of the 8 concentrations (5.6 μg up to 720 μg/ml) of DLHW (SEQ ID NO:2) and the test matrix.

TABLE 2

Effects of peptides analysed and the test matrix added at 1DIV on viability of cortical neurons obtained in the 2% Low Serum Assay with the MTT method. Results shown as mean, standard deviation and standard error mean (SEM) of the optical densities (OD):

|  | 0 | 5.6 | 11.25 | 22.5 | 45 | 90 | 180 | 360 | 720 μg/ml |
|---|---|---|---|---|---|---|---|---|---|
| | | | | mean | | | | | |
| DLHW (SEQ ID NO: 2) | 0.063 | 0.062 | 0.062 | 0.085 | 0.136 | 0.217 | 0.272 | 0.254 | 0.257 |
| NIVTPR (SEQ ID NO: 3) | 0.069 | 0.068 | 0.069 | 0.068 | 0.068 | 0.066 | 0.064 | 0.060 | 0.058 |
| HGFLPR (SEQ ID NO: 4) | 0.068 | 0.068 | 0.069 | 0.069 | 0.067 | 0.070 | 0.067 | 0.064 | 0.058 |
| NMVPFPR (SEQ ID NO: 5) | 0.062 | 0.061 | 0.060 | 0.057 | 0.057 | 0.056 | 0.055 | 0.055 | 0.057 |
| test matrix | 0.082 | 0.082 | 0.085 | 0.085 | 0.088 | 0.090 | 0.088 | 0.082 | 0.069 |
| | | | | stand. dev. | | | | | |
| DLHW (SEQ ID NO: 2) | 0.005 | 0.004 | 0.006 | 0.031 | 0.070 | 0.068 | 0.030 | 0.015 | 0.038 |
| NIVTPR (SEQ ID NO: 3) | 0.004 | 0.003 | 0.005 | 0.005 | 0.004 | 0.004 | 0.004 | 0.005 | 0.003 |
| HGFLPR (SEQ ID NO: 4) | 0.005 | 0.004 | 0.004 | 0.005 | 0.004 | 0.005 | 0.004 | 0.005 | 0.007 |
| NMVPFPR (SEQ ID NO: 5) | 0.004 | 0.003 | 0.004 | 0.004 | 0.003 | 0.004 | 0.002 | 0.002 | 0.003 |
| test matrix | 0.014 | 0.015 | 0.016 | 0.016 | 0.019 | 0.017 | 0.015 | 0.015 | 0.010 |
| | | | | sem | | | | | |
| DLHW (SEQ ID NO: 2) | 0.001 | 0.001 | 0.002 | 0.011 | 0.025 | 0.024 | 0.011 | 0.005 | 0.013 |
| NIVTPR (SEQ ID NO: 3) | 0.001 | 0.001 | 0.002 | 0.002 | 0.002 | 0.001 | 0.001 | 0.002 | 0.001 |
| HGFLPR (SEQ ID NO: 4) | 0.001 | 0.001 | 0.001 | 0.002 | 0.002 | 0.002 | 0.002 | 0.002 | 0.003 |
| NMVPFPR (SEQ ID NO: 5) | 0.001 | 0.001 | 0.001 | 0.001 | 0.001 | 0.001 | 0.001 | 0.001 | 0.001 |
| test matrix | 0.004 | 0.005 | 0.006 | 0.006 | 0.007 | 0.006 | 0.005 | 0.005 | 0.004 |

Values represent the ODs as mean, standard deviation and SEM from four independent experiments performed at four days with two identical 96-well plates ($n \geq 8$ for each peptide and test matrix concentration and for controls). The unlesioned control is represented by 0 and did not receive neither a peptide nor the test matrix.

TABLE 3

Effects of the peptides analysed and the test matrix added at 1DIV on viability of cortical neurons obtained in the 2% Low Serum Assay with the MTT method. Results shown as mean, standard deviation and SEM of the data in % (control is 100%; see also FIG. 1 for DLHW):

|  | 0 | 5.6 | 11.25 | 22.5 | 45 | 90 | 180 | 360 | 720 µg/ml |
|---|---|---|---|---|---|---|---|---|---|
| | | | | mean | | | | | |
| DLHW (SEQ ID NO: 2) | 100.00 | 97.85 | 97.68 | 134.51 | 213.12 | 341.82 | 429.54 | 401.23 | 406.75 |
| NIVTPR (SEQ ID NO: 3) | 100.00 | 98.92 | 100.32 | 98.70 | 98.75 | 95.12 | 92.28 | 86.60 | 83.13 |
| HGFLPR (SEQ ID NO: 4) | 100.00 | 100.07 | 101.16 | 101.16 | 98.95 | 102.25 | 99.14 | 94.53 | 85.71 |
| NMVPFPR (SEQ ID NO: 5) | 100.00 | 98.06 | 95.77 | 90.76 | 90.55 | 89.54 | 87.76 | 87.79 | 91.24 |
| test matrix | 100.00 | 99.94 | 103.17 | 103.51 | 107.12 | 109.78 | 106.87 | 99.34 | 85.08 |
| | | | | stand. dev. | | | | | |
| DLHW (SEQ ID NO: 2) | 5.80 | 4.12 | 8.85 | 47.75 | 107.35 | 102.95 | 45.65 | 25.04 | 56.18 |
| NIVTPR (SEQ ID NO: 3) | 5.42 | 3.70 | 6.43 | 6.75 | 6.37 | 4.91 | 6.43 | 7.46 | 3.32 |
| HGFLPR (SEQ ID NO: 4) | 7.01 | 4.97 | 5.08 | 6.52 | 5.67 | 5.45 | 5.71 | 6.49 | 10.29 |
| NMVPFPR (SEQ ID NO: 5) | 5.44 | 5.79 | 5.77 | 5.12 | 3.99 | 5.00 | 2.97 | 2.41 | 4.92 |
| test matrix | 10.44 | 10.46 | 10.93 | 12.99 | 15.63 | 14.24 | 11.07 | 11.44 | 12.54 |
| | | | | sem | | | | | |
| DLHW (SEQ ID NO: 2) | 1.45 | 1.46 | 3.13 | 16.88 | 37.96 | 36.40 | 16.14 | 8.85 | 19.86 |
| NIVTPR (SEQ ID NO: 3) | 1.36 | 1.31 | 2.27 | 2.39 | 2.25 | 1.73 | 2.27 | 2.64 | 1.17 |
| HGFLPR (SEQ ID NO: 4) | 1.75 | 1.76 | 1.80 | 2.31 | 2.00 | 1.93 | 2.02 | 2.29 | 3.64 |
| NMVPFPR (SEQ ID NO: 5) | 1.36 | 2.05 | 2.04 | 1.81 | 1.41 | 1.77 | 1.05 | 0.85 | 1.74 |
| test matrix | 2.61 | 3.70 | 3.87 | 4.59 | 5.53 | 5.03 | 3.92 | 4.04 | 4.43 |

Values represent the viability in % as mean, standard deviation and SEM from four independent experiments performed at four days with two identical 96-well plates (n≧8 for each peptide and test matrix concentration and for controls). The unlesioned control is represented by 0 and did not receive any peptide and test matrix.

While in table 2 results are shown as mean, standard deviation and s.e.m. of the optical densities (OD), table 3 illustrates the results relative to the untreated control, as percentage, whereby the mean of the untreated control has been taken as 100%. Fig. 1 corresponds to the results shown in table 3 for DLHW (SEQ ID NO: 2).

FIG. 1 shows the effects of the effective peptide, DLHW (SEQ ID NO: 2) in comparison to the test matrix. The maximum effect of 430% can be obtained with a concentration of 360µg/ml DLHW (SEQ ID NO: 2), but even in higher concentrations effects are still in a range of 300% above the control level. In contrast thereto, the other peptides analysed did not show any significant effect.

In table 5 the main effects obtained with DLHW (SEQ ID NO: 2) and the test matrix are outlined. Again summarizing the results described above.

TABLE 4

Results of the statistical analysis —p-values: In the upper part of the table p-values displaying the differences between the untreated control and the different concentrations of the peptides and test matrix are shown.
Differences versus conc and control

|  | 5.6 | 11.25 | 22.5 | 45 | 90 | 180 | 360 | 720 µg/ml |
|---|---|---|---|---|---|---|---|---|
| DLHW (SEQ ID NO: 2) | 0.1945449 | 0.484933 | 0.0802617 | 0.0205037 | 0.0002919 | 1.672E−07 | 4.603E−09 | 1.1428E−06 |
| test matrix | 0.9878519 | 0.4414904 | 0.4712104 | 0.2391877 | 0.0934033 | 0.1238825 | 0.8761068 | 0.01191905 |

Differences between the different values are considered to be significant when p≦0.05. Values for calculation of differences were obtained from four experiments performed at four days with two identical 96-well plates (n≧8 for DLHW (SEQ ID NO:2) and test matrix concentration and for controls). The unlesioned control did not receive any peptide and test matrix.

TABLE 5

Summary of the effects of the peptides and the test matrix added at 1DIV on viability of cortical neurons obtained with the MTT method.

| Name | effective dose range | most effectice concentration | maximum effect in % | effect beyond control |
|---|---|---|---|---|
| DLHW (SEQ ID NO: 2) | 45-702 µg/ml | 180 µg/ml | 430% | 430% |
| NIVTPR (SEQ ID NO: 3) | — | — | — | — |
| HGFLPR (SEQ ID NO: 4) | — | — | — | — |
| NMVPFPR (SEQ ID NO: 5) | — | — | — | — |
| test matrix | — | — | — | — |

7. Summary of the Experimental Data

Summarizing the possible neurotrophic/neuroprotective effects of the DLHW (SEQ ID NO: 2) obtained in a 2% low serum assay it can be stated that DLHW (SEQ ID NO: 2) significantly increases neuronal viability compared to the untreated control. Furthermore, it could be clearly shown that peptides having another amino acid sequence than DLHW (SEQ ID NO: 2) do not exhibit neurotrophic and neuroprotective properties.

The invention claimed is:

1. A neuroprotective compound consisting of the amino acid sequence DLHW (SEQ ID NO: 2).

2. The composition of claim 1, wherein the composition is adapted for intravenous, intramuscular, spinal, epidural, transdermal, parenteral, oral, enteral, intranasal or rectal administration.

3. A pharmaceutical composition comprising a neuroprotective compound consisting of the amino acid sequence DLHW (SEQ ID NO: 2).

4. The composition of claim 3, further comprising a pharmaceutically acceptable excipient and/or carrier.

5. The composition of claim 3, further comprising at least one additional pharmaceutically active component.

6. The composition of claim 5, wherein the at least one pharmaceutically active component is tetrapeptide L-alanyl-L-glutamyl-L-asparagyl-L-proline or cerebrolysin.

7. The composition of claim 3, wherein the compound is comprised in the composition in an amount of 0.1 μg/g to 100 mg/g.

8. The composition of claim 7, wherein the compound is comprised in the composition in an amount of 1 μg to 80 mg/g.

* * * * *